United States Patent
Troedsson et al.

(10) Patent No.: US 10,226,032 B2
(45) Date of Patent: Mar. 12, 2019

(54) METHOD FOR FARMING ASCIDIANS

(75) Inventors: Christofer Troedsson, Paradis (NO);
Eric Thompson, Paradis (NO);
Christoffer Schander, Bergen (NO);
Jean-Marie Bouquet, Bergen (NO);
Thorolf Magnesen, Blomsterdalen (NO); Jiebing Li, Bandhagen (SE)

(73) Assignee: BERGEN TEKNOLOGIOVERFORING AS, Bergen (NO)

( * ) Notice: Subject to any disclaimer, the term of this patent is extended or adjusted under 35 U.S.C. 154(b) by 290 days.

(21) Appl. No.: 13/704,807

(22) PCT Filed: Jun. 17, 2011

(86) PCT No.: PCT/IB2011/052652
§ 371 (c)(1),
(2), (4) Date: Sep. 23, 2013

(87) PCT Pub. No.: WO2011/158215
PCT Pub. Date: Dec. 22, 2011

(65) Prior Publication Data
US 2014/0020283 A1   Jan. 23, 2014

(30) Foreign Application Priority Data

Jun. 17, 2010   (GB) .................................. 1010176.4

(51) Int. Cl.
*A01K 61/54*   (2017.01)
*A01K 61/10*   (2017.01)
(Continued)

(52) U.S. Cl.
CPC .............. *A01K 61/54* (2017.01); *A01K 61/10* (2017.01); *C07C 29/095* (2013.01);
(Continued)

(58) Field of Classification Search
CPC .... A01K 61/00; A01K 61/002; A01K 61/005; A01K 61/006; A01K 61/007; A01K 80/00
(Continued)

(56) References Cited

U.S. PATENT DOCUMENTS 3,675,626 A * 7/1972 Down ........................ 119/238
3,741,159 A * 6/1973 Halaunbrenner .... A01K 61/002
119/240

(Continued)

FOREIGN PATENT DOCUMENTS

| CN | 1208551 A | 2/1999 |
|---|---|---|
| CN | 101641287 A | 2/2010 |

(Continued)

OTHER PUBLICATIONS

Joly, Kano Matsuoka, Auger, Hirayama, Satoh, Awazu, Legendre, Sasakura. "Culture of Ciona intestinalis in Closed Systems." Developmental Dynamics 236:1832-1840, Feb. 19, 2007.*

(Continued)

*Primary Examiner* — Magdalena Topolski
(74) *Attorney, Agent, or Firm* — Nixon & Vanderhye P.C.

(57) ABSTRACT

This invention relates to the use of a tunicate or an extract obtained from a tunicate for the production of one or more biofuel selected from an alcohol and biodiesel. The invention also relates to a method for producing a biofuel from a tunicate wherein the biofuel is selected from an alcohol and biodiesel and wherein said method comprises the steps of: (a)(i) subjecting said tunicate or one or more polysaccharides extracted from said tunicate to enzymatic or acid hydrolysis to form a hydrolysate containing one or more monosaccharides and (ii) fermenting said one or more monosaccharides to form an alcohol; or (b)(i) extracting lipids/fatty acids from said tunicate and (ii) converting said lipids/fatty acids into biodiesel by transesterification or (Continued)

alcoholysis or (iii) subjecting said tunicate to transesterification or alcoholysis thereby converting lipids/fatty acids present in said tunicate into biodiesel.

22 Claims, 6 Drawing Sheets

(51) Int. Cl.
*C10L 1/02* (2006.01)
*C12P 7/10* (2006.01)
*C12P 7/64* (2006.01)
*C07C 29/09* (2006.01)
*C07C 29/147* (2006.01)
*A01K 61/00* (2017.01)

(52) U.S. Cl.
CPC ............ *C07C 29/147* (2013.01); *C10L 1/026* (2013.01); *C12P 7/10* (2013.01); *C12P 7/649* (2013.01); *A01K 61/00* (2013.01); *C10L 1/02* (2013.01); *Y02A 40/81* (2018.01); *Y02A 40/822* (2018.01); *Y02E 50/13* (2013.01); *Y02E 50/16* (2013.01); *Y02E 50/17* (2013.01); *Y02P 30/20* (2015.11)

(58) Field of Classification Search
USPC ....... 119/241, 240, 239, 238, 223, 222, 209, 119/208, 200
IPC ...................................................... A01K 61/00
See application file for complete search history.

(56) References Cited

U.S. PATENT DOCUMENTS

| 3,889,639 | A | * | 6/1975 | Day ..................... A01K 61/005 119/211 |
| 4,036,176 | A | * | 7/1977 | McCarty et al. ............. 119/207 |
| 4,916,845 | A | * | 4/1990 | Aydelette, Sr. ........ A01K 97/02 43/4 |
| 5,315,779 | A | * | 5/1994 | Fussell ................................ 43/4 |
| 5,515,813 | A | * | 5/1996 | Wilkerson ........... A01K 61/007 119/223 |
| 6,089,191 | A | * | 7/2000 | Calinski ............... A01K 61/006 119/208 |
| 6,520,116 | B1 | * | 2/2003 | Jefferds ......................... 119/238 |
| 6,539,894 | B1 | * | 4/2003 | Byrne .................. A01K 61/002 119/234 |
| 6,962,130 | B1 | * | 11/2005 | Kennedy ....................... 119/221 |
| 6,978,735 | B1 | * | 12/2005 | Yeager .......................... 119/221 |
| 7,587,991 | B2 | * | 9/2009 | Buck et al. .................... 119/239 |
| 8,640,651 | B2 | * | 2/2014 | Ewald ........................... 119/221 |
| 2003/0111020 | A1 | | 6/2003 | Targotay et al. |
| 2003/0177982 | A1 | * | 9/2003 | Jenkins .................. A01K 61/70 119/221 |
| 2006/0288636 | A1 | | 12/2006 | Iijima et al. |
| 2008/0113413 | A1 | | 5/2008 | Nobles et al. |
| 2009/0320766 | A1 | | 12/2009 | Calinski |
| 2010/0139265 | A1 | | 6/2010 | Stroiazzo Mougin |
| 2011/0017144 | A1 | * | 1/2011 | Calinski ................. A01K 61/54 119/200 |
| 2011/0275118 | A1 | | 11/2011 | De Crecy |
| 2013/0118413 | A1 | * | 5/2013 | Bennett ......................... 119/200 |
| 2013/0298841 | A1 | * | 11/2013 | Vadassery et al. ........... 119/223 |

FOREIGN PATENT DOCUMENTS

| JP | 05207831 A * | 8/1993 |
| JP | 2004089008 A * | 3/2004 |
| JP | 2005-060597 | 3/2005 |
| JP | 2006067952 A * | 3/2006 |
| JP | 2008271960 A * | 11/2008 |
| JP | 2009-100713 | 5/2009 |
| JP | 2010-124774 | 6/2010 |
| JP | 2010148521 A * | 7/2010 |
| KR | 84-653720-1984-00006537 | 12/1984 |
| WO | WO 99/56535 | 11/1999 |
| WO | WO 2005/017075 A1 | 2/2005 |
| WO | WO 2008/042975 | 4/2008 |
| WO | WO 2008/087238 | 7/2008 |
| WO | WO 2010/036333 | 4/2010 |
| WO | WO 2010/042842 | 4/2010 |
| WO | WO 2010/048568 | 4/2010 |
| WO | WO 2010/074577 | 7/2010 |
| WO | WO 2011/028163 | 3/2011 |

OTHER PUBLICATIONS

Uwabe, Michiyoshi. "Air Feeder Utilizing Windmill for Culturing Fisheries Animal and Plant." JP-05207831 English translation.*
Uwabe, Michiyoshi. "Air Feeder Utlizing Windmill for Culturing Fisheries Animal and Plant" JP-05207831. Human Translation.*
Hisami, JP 2008-271960 English translation. (Year: 2008).*
International Search Report for PCT/IB2011/052652 dated Dec. 29, 2011.
Search Report for GB 1010176.4 dated Oct. 15, 2010.
M. Kelly et al., "The Potential of Marine Biomass for Anaerobic Biogas Production", Marine Estate Research Report, Jan. 1, 2008, 49 pages.
Office Action in related Japanese Patent Application No. 2013-514835; dated Jul. 30, 2015; in Japanese with English Translation.
Chinese Notification of First Office Action and English translation thereof dated Nov. 1, 2017 in Chinese Application 201510259518.1.
Karunasagar et al, "Marine Biotechnology: A Natural Biorefinery Source of Marine Products and By-products for Human Welfare", *Asian Biotechnology and Development Review*, vol. 10, Nos. 1 and 2, pp. 89-102, Feb. 2008.
Korean Notification of Grounds for Rejection dated Jul. 10, 2017 in Korean Application 10-2013-7001266.
Wu Moucheng, editor-in-chief, "Biodiesel", Chemical Industry Press, pp. 26-37, Jan. 31, 2008 with partial English translation.
Edited by Wang Changhai, "Introduction to Marine Biochemical Engineering", Chemical Industry Press, pp. 240-246, Sep. 30, 2004 with partial English translation.

* cited by examiner (i)

(ii)

METHOD FOR FARMING ASCIDIANS

This application is the U.S. national phase of International Application No. PCT/IB2011/052652 filed 17 Jun. 2011 which designated the U.S. and claims priority to GB 1010176.4 filed 17 Jun. 2010, the entire contents of each of which are hereby incorporated by reference.

The present invention relates to the use of a tunicate or an extract obtained from a tunicate for the production of one or more biofuels selected from an alcohol and biodiesel. The present invention also relates to a method for producing a biofuel selected from an alcohol and biodiesel from a tunicate and to a method of farming ascidians.

BACKGROUND TO THE INVENTION

The depletion of global fossil fuel supplies and its effect on the global climate systems has prompted a drive to find alternative energy sources, in particular renewable energy sources. One promising alternative to fossil fuel is ethanol as it can be produced from renewable sources and has lower emissions than fossil fuel. Currently sources of biomass for the production of ethanol are plant-derived, with major sources including terrestrial food crops such as sugar cane and corn. Non-food crops such as wood and Miscanthus are also used as sources of biomass for the production of ethanol. Another alternative to fossil fuel is biodiesel which also can be produced from renewable energy sources. Currently, the major feedstocks for biodiesel production include palm oil and coconut. However, a major problem with the aforementioned sources of biomass/feedstock is that they compete directly for arable land essential for food production. Thus, as the global population rises, use of such terrestrial sources for biofuel production could lead to food shortages and food price rises. Waste from food crops such as stalks of wheat and corn are also used as biomass for the production of ethanol and, although, this source of biomass does not suffer the problem with competing directly with the food supply, it is insufficient on its own to meet global demand. In recent years, attention has also been directed to the production of biofuels such as ethanol from algae. However difficulties have been encountered in extraction processes and commercial realisation has yet to occur. In addition, large bioreactors are required to make sufficient quantities of algae and, to increase the efficiency, research is currently focused on genetically modified organisms which adds extra constraints on the handling process.

Renewable energy sources need to fulfil requirements which include: (i) capability of being produced in large quantities; (ii) being non-competitive with food supply; and (iii) having minimal environmental impact. There is a strong need for a renewable energy source which addresses the above problems and meets the above requirements.

Tunicates are a group of underwater filter feeders found globally in most marine habitats. Ascidians are the most commonly known class of tunicates. Their most common use is as a model organism in evolutionary developmental biology research. Their embryonic development is simple, rapid and easily manipulated and thus they make good models for studying the fundamental development processes of chordates. Tunicates are the only animals that synthesise cellulose. It is known to extract cellulose from ascidians and to use same in the manufacture of building materials (KR2000-0000303 and JP09-157304). There have been no reports or studies on the development of tunicates for producing biofuels such as alcohols and biodiesel until now.

STATEMENT OF INVENTION

A first aspect of the invention relates to the use of a tunicate or an extract obtained from a tunicate for the production of one or more biofuels selected from an alcohol and biodiesel.

A second aspect of the invention relates to a method for producing a biofuel from a tunicate wherein said biofuel is selected from an alcohol and biodiesel and wherein said method comprises:
  (a) (i) subjecting said tunicate or one or more polysaccharides extracted from said tunicate to enzymatic or acid hydrolysis to form a hydrolysate containing one or more monosaccharides and (ii) fermenting said one or more monosaccharides to form an alcohol; or
  (b) (i) extracting lipids/fatty acids from said tunicate and (ii) converting said lipids/fatty acids into biodiesel by transesterification or alcoholysis.

The second aspect of the invention also relates to a method for producing biodiesel from a tunicate wherein said method comprises converting lipids/fatty acids present in the tunicate into biodiesel by subjecting the tunicate to transesterification or alcoholysis.

A third aspect of the invention relates to a method of producing a first biofuel from a tunicate according to the method described in the preceding paragraph and additionally producing a second biofuel from said tunicate according to the method described in the preceding paragraph wherein the first and second biofuels are different and are selected from an alcohol and biodiesel.

A fourth aspect of the invention relates to a method for farming ascidians comprising the steps of:
  (a) colonising surfaces of a sub-sea structure with ascidians; and
  (b) harvesting said ascidians from said structure,
wherein said structure comprises a plurality of elongate members having colonisation surfaces and said structure defines a three-dimensional sub-sea region arranged to support tunicate colonisation.

The invention relates to a new source of biomass for the production of the biofuels which are alcohols and biodiesel. Tunicates are opportunistic and have very high growth potential and therefore can potentially provide large quantities of biomass; they do not require arable land for growth and so do not compete with the production of terrestrial food crops; and their farming has secondary positive effects such as improvement of water quality, particularly in areas subject to undesirable levels of eutrophication due to terrestrial run-off. Thus this new source of biomass meets the requirements mentioned above for a renewable energy source.

FIGURES

FIG. 6(i) is a photograph of cellulose obtained from a C. intestinalis sample as described in the examples, under microscopy (×40).

DETAILED DESCRIPTION

Figure 1:
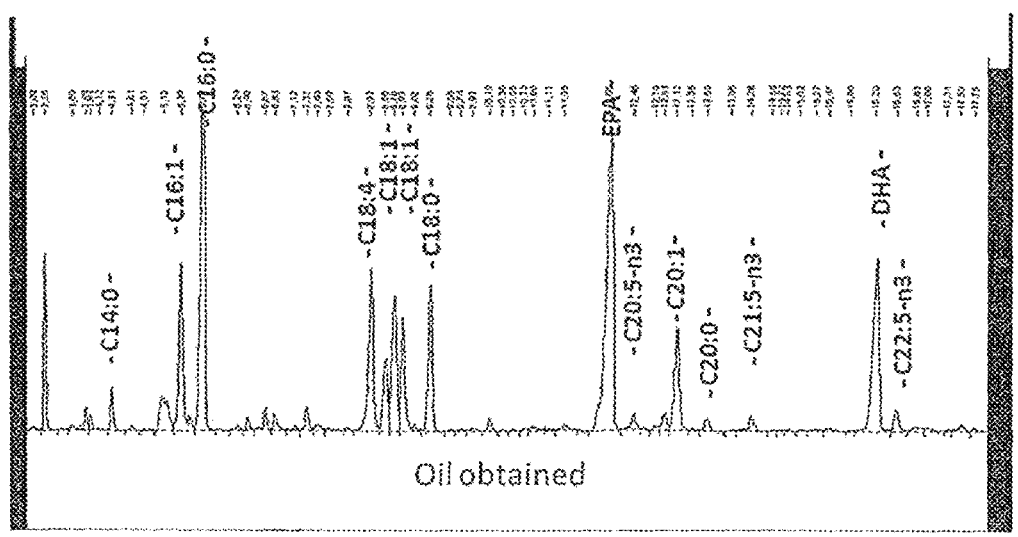
FIG. 1 is a gas chromatogram spectrum showing the fatty acid composition of a *C. intestinalis* sample.

A first aspect of the invention relates to the use of a tunicate or extract obtained from a tunicate for the production of one or more biofuels selected from an alcohol and biodiesel.

Tunicates

Tunicates are found globally in most marine habitats. Tunicates are the only animals that synthesise cellulose. Cellulose represents a significant proportion of the animal's biomass[1,2]. Tunicates have high growth potential, a feature which can contribute to large blooms during the year and result in significant cellulose resources. This makes them particularly suitable as a renewable energy resource.

Within the subphylum Tunicata, there are three classes: ascidians, thaliaceans and larvaceans[3]. In the invention, the tunicate is selected from ascidians, thaliaceans or larvaceans. Preferably, the tunicate is an ascidian. Ascidians are also commonly known as sea squirts. Many species of ascidian are opportunistic with a free living pelagic larval stage and will go through a metamorphosis as they settle on a new surface in the marine environment, e.g. the surface of the hull of a ship. Due to their opportunistic behaviour they are often the first animals to colonize the surfaces of a new submerged structure. They are therefore easy to harvest.

There are many species of ascidians, for example, *Aplidium glabrum, Ascidia sydneiensis, Ascidia mentula, Ascidiella aspersa, Botrylloides violaceus, Bottyllus schlloseri, Ciona savignyi, Didemnum candidum, Didemnum vexillum, Diplosoma listerianum, Eusynstyela tincta, Herdmania pallida, Lissoclinum fragile, Microcosmus exasperatus, Microcosmus squamiger, Molgula manhattensis, Perophora japonica, Phallusia nigra, Styela canopus, Styela clava, Trididemnum solidus* and *Ciona intestinalis*. Among the ascidians, *C. intestinalis* is the most dominant species in Scandinavian waters. It is also the most studied species, primarily because of its use as a model organism in evolutionary developmental biology[4]. *C. intestinalis* is hermaphroditic, spawning freely into the water column where fertilisation takes place. The larvae are free swimming, non-feeding and will adhere to any suitable surface and undergo metamorphosis within 1-5 days dependent on the temperature[5,6]. Cellulose is produced in the tunic of both the larval and adult stages. In larvae it serves primarily a protective function but is also involved in controlling the order of events during metamorphosis leading to the juvenile and adult fore[7,8]. In adults, cellulose is a structural component of the tunic which surrounds the entire animal and grows in concert with the rest of the body. It is also present in the tunic chord which connects the tunic and mantle[9]. Along the Scandinavian coasts, larval settling occurs continuously throughout the year. In a preferred embodiment of the present invention the tunicate is *C. intestinalis*.

As used herein, a tunicate refers to the whole or part of the body of a tunicate.

As used herein, an extract obtained from a tunicate refers to material rich in one type of substance obtained from said tunicate. Extracts obtained from a tunicate include material obtained by processing a tunicate which is rich in: one or more monosaccharides; a polysaccharide, e.g. cellulose; and/or lipids/fatty acids.

In the invention a tunicate or the extract obtained from a tunicate is used as biomass or raw material for the production of the biofuels described herein.

As used herein the term "a tunicate" can be replaced by "one or more tunicates" or "tunicates".

Biofuel

As used herein, a biofuel is a biofuel selected from an alcohol and biodiesel, preferably selected from ethanol and fatty acid alkyl esters.

Alcohol

In one aspect, the invention relates to the use of a tunicate or extract obtained from a tunicate for the production of an alcohol. Preferably the alcohol is a $C_1$-$C_4$ alcohol, i.e. methanol, ethanol, propanol or butanol. More preferably the alcohol is ethanol.

The present studies have found a yield of 8.8 weight % $C_6$ sugars (6.7 weight % cellulose, 2.1 weight % mannose and galactose) and 0.4 weight % of $C_5$ sugars for the tunicate *C. intestinalis*. Cellulose can be converted to ethanol either by enzymatic or acid hydrolysis, followed by fermentation[10 to 15]. The present studies have found that the cellulose derived from *C. intestinalis* is more crystalline and smaller in molecular size than wood cellulose. Therefore this cellulose is more easily hydrolysed by either acidic or enzymatic hydrolysis to glucose for fermentation to ethanol. As a result, production of ethanol from this cellulose will be simpler and cheaper than that from wood.

The potential for ethanol production from this species can be estimated as follows. From literature, it is known that a 100 mm long *C. intestinalis* has a dry weight of 0.6 g[16]. *C. intestinalis* is often found at densities reaching 3000 individuals per m$^2$ of ocean floor. This amount of ascidians will weigh 1.8 kg/m$^2$ (3,000 individuals/m$^2$×0.0006 kg/individual=1.8 kg of ascidians/m$^2$). At a yield of 8.8 weight % $C_6$ sugars, 1.8 kg of ascidians will yield 0.16 kg of $C_6$ sugars (0.088×1.8 kg=0.16 kg of $C_6$ sugars). Assuming a yield of 0.64 l ethanol per kg of $C_6$ sugar, 0.16 kg of $C_6$ sugars will yield 0.10 l of ethanol (0.16×0.64=0.10 l of ethanol). This gives a yield of ethanol of 0.10 l/m$^2$ or 1,000 l/hectare of ocean floor.

The above calculation is based on one harvest. As it is possible to harvest *C. intestinalis* at least twice a year[17], there is potential for an annual ethanol yield of at least 2,000 l/hectare of ocean floor. This calculation is made for 2-dimensional farming, e.g. on the ocean floor. As ascidians can be farmed in three dimensions in the ocean water column, the potential ethanol yield per hectare of ocean floor/ocean surface is much greater. Ascidians are not restricted to the photic zone and therefore high growth rates can be obtained down to depths as low as 60 or 70 m. Taking a situation where ascidians are grown on in submerged rods that are 20 m in length and 0.4 m in diameter (giving a surface area of 25.12 m$^2$ per rod) and which are spaced 1 m apart throughout 1 hectare (i.e. 10,000 rods). This provides 251,200 m$^2$ of surface area for ascidian growth per hectare of ocean surface. This, based on the above calculations, in turn, could yield an annual production of about 50,900 l of ethanol per hectare of ocean surface. This means that 1 hectare of ocean surface has the potential to provide at least about 50,900 l of ethanol annually. Besides $C_6$ sugars, a yield of 0.4 weight % of $C_5$ sugars is possible from the ascidian C. intestinalis. $C_5$ sugars can be fermented to ethanol, adding 4.5% more ethanol to that obtained from $C_6$ sugars (i.e. based on the above model, giving an annual production of 1.045×50, 900=53,190 l ethanol).

The present studies have shown that the yield can be much greater than the above estimate. The present studies have shown that C. intestinalis can grow to about 31 g (1.37 g dry weight) after 6 months of growth. Further, using elongated members which support a plurality of colonisation surfaces in the form of plates as described herein, densities of 9690 individuals per $m^2$ can be attained. In a 3-dimensional farming model, assuming 3 plates per meter of length on a 20 meter rope and a plate surface area of 0.2 $m^2$, there will be a surface area of 12 $m^2$ per elongated member in the sea, or 120,000 $m^2$ per hectare if the elongated members are spaced 1 m apart. Assuming 2 harvests per year, the annual ethanol yield per hectare will be about 180,000 l using the same calculation as above (9690 individuals/$m^2$×0.00137 kg×0.088 C6 sugar×0.64 l ethanol per kg sugar×120,000 $m^2$×2 harvests per year=180,000 l of ethanol), or 188,000 l annually including the contribution from C5 sugars.

The potential ethanol yield from tunicates can be compared with the annual yields from crops traditionally used as biomass for the production of ethanol in the table below:

TABLE 1

Annual ethanol yield from various crops[18]

| Crop | Annual Yield (l/hectare) |
|---|---|
| Miscanthus | 7,300 |
| Switchgrass | 3,100-7,600 |
| Poplar | 3,700-6,000 |
| Sugar cane | 6,800-8,000 |
| Sweet sorghum | 7,000 |
| Corn | 3,100-4,100 |

Thus the amount of ethanol per hectare of ocean surface produced from tunicates has the potential to greatly exceed that produced from terrestrial crops per hectare of arable land and by one order of magnitude in some cases.

Preferably the invention relates to the use of a tunicate as biomass for the production of an alcohol. In one aspect, the invention relates to a method for producing an alcohol from a tunicate wherein said method comprises:
(i) subjecting said tunicate to enzymatic or acid hydrolysis to form a hydrolysate containing one or more monosaccharides; and
(ii) fermenting said one or more monosaccharides to form an alcohol.

In this aspect of the invention, the tunicate itself is subjected to enzymatic or acid hydrolysis and no extraction of polysaccharides or monosaccharides from the tunicate is necessary.

The tunicate can be in the form of the whole of the body of the tunicate or it can be in the form of part of the body of a tunicate, preferably the tunic which has been isolated from the rest of the tunicate body. The tunicate can, for example, be freshly harvested or thawed out from a frozen supply. Preferably the tunicate is washed to remove sea salts. Preferably this washing is carried out on wet tunicate, i.e. tunicate that has not be subjected to drying and preferably the washing is carried out with deionised or fresh water. This advantageously reduces the ash content of the resultant tunicate material.

Before subjecting the tunicate to enzymatic or acid hydrolysis, the tunicate is preferably dried. Preferably, the invention relates to a method for producing an alcohol from a tunicate wherein said method comprises:
(i) drying said tunicate;
(ii) subjecting said dried tunicate to enzymatic or acid hydrolysis to form a hydrolysate containing one or more monosaccharides; and
(iii) fermenting said one or more monosaccharides to form an alcohol.

Drying can be carried out by any means known in the art. Preferably the tunicate is dried to a dryness content (also referred to herein as dryness) of above 50%, more preferably to above 70%, more preferably to above 80%, more preferably to above 85% and even more preferably to above 90%. As used herein dryness content is a measure of the dry weight of the tunicate material. It is calculated after drying the tunicate material either by oven heating at 105° C. overnight (on gram-scale of sample) or by infra-red heating at 105° C. until a constant weight is reached (on 300 mg-scale of sample) and is the weight percent of resultant dried material based on the weight of the wet tunicate material prior to the drying. The tunicate can be dried by pressing it to remove some of the water, laying it on a heated floor to dry it to, for example, about 39% dryness. Then the tunicate can be transferred to an oven, for example, heated to 130-150° C., where it is dried to, for example, about 89% dryness. Alternatively, the tunicate can be dried by freeze-drying or dried by spray-drying, for example, at temperatures of greater than 100° C. over a time scale in seconds. The use of dried tunicate has the advantage of minimising inhibitive effects on any subsequent enzymatic hydrolysis. In one embodiment, the dried tunicate material can be mechanically broken down, by milling for example.

In this aspect of the invention, the dried tunicate material can be subjected to enzymatic or acid hydrolysis to form a hydrolysate containing one or more monosaccharides. The hydrolysate can then be subjected to fermentation to produce an alcohol.

Besides cellulose, tunicates also comprise $C_6$ sugars such as mannose and galactose and can comprise one or more $C_5$ sugars such as xylose and arabinose. Dried tunicate comprises polysaccharides such as cellulose and other polysaccharides or glycoprotein composed of glucose and other $C_6$ sugars such as mannose and galactose as well as one or more $C_5$ sugars such as xylose and arabinose.

When the tunicate is subjected to enzymatic or acid hydrolysis to form a hydrolysate containing one or more monosaccharides, the hydrolysate may contain monosaccharides that already existed in the tunicate as well as monosaccharides that have been produced by the hydrolysis of cellulose and other components.

The methods of enzymatic and acid hydrolysis followed by fermentation utilised in the present invention are not limited and include any method known to those in the art and are described in the following publications:
Li J, Lennholm H, Henriksson G, Gellerstedt G (2000a). Bio-refinery of lignocellulosic materials for ethanol production. I. Quantification of carbohydrates, 13$^{th}$ International Symposium on Alcohol Fuels (ISAF XIII) (Stockholm, 3-6 Jul. 2000), proceedings (Vol. I), Number 6;

Li J, Lennholm H, Henriksson G, Gellerstedt G (2000b). Bio-refinery of lignocellulosic materials for ethanol production. II. Fundaments and strategic design of steam explosion, 1$^{st}$ World Conference and Exhibition on Biomass for Energy and Industry (Seville, 5-9 June, 2000), proceedings, 767-770;

Li J, Lennholm H, Henriksson G, Gellerstedt G (2001). Bio-refinery of lignocellulosic materials for ethanol production. III. Evaluation of steam explosion by kappa number determination, 7$^{th}$ Brazilian Symposium on the Chemistry of Lignins and Other Wood Components, (Belo Horizonte, 3-5 Sep. 2001), proceedings (oral presentation), 423-430;

Li J, Lennholm H, Henriksson G, Gellerstedt G (2002). Bio-refinery of lignocellulosic materials for ethanol production. IV. Manufacture of high value by-products for improvement of process economic feasibility, 2$^{nd}$ International Symposium on Emerging Technologies of Pulping & Papermaking, (Guangzhou, 9-11 Oct. 2002), proceedings, 82-90;

Lin Y, Tanaka S (2006). Ethanol fermentation from biomass resources: current state and prospects. *Applied Microbiology and Biotechnology* 69(6): 627-642; and Hahn-Hägerdal B, Galbe M, Gorwa-Grauslund M F, Lidén G, Zacchi G (2006). Bio-ethanol—the fuel of tomorrow from the residues of today. *Trends in Biotechnology* 24(12): 549-556.

In one embodiment, the method of the invention involves acid hydrolysis of the tunicate. Preferably sulphuric acid is used, for example concentrated sulphuric acid such as 72-74% $H_2SO_4$.

In one embodiment, the method of the invention involves enzymatic hydrolysis of the tunicate. One or more enzymes can be used including enzymes for converting polysaccharides into monosaccharides. Preferably the one or more enzymes convert the cellulose into glucose, for example cellulase and glucosidase.

In a preferred embodiment, the hydrolysate comprises glucose and this is fermented into ethanol using *Saccharomyces cerevisiae* strains, commonly known as baker's yeast.

Recovery of the alcohol, preferably ethanol, can be achieved by distillation to separate the alcohol, preferably ethanol, from the other components of the fermentation broth and dehydration to remove any residual water from the alcohol, preferably ethanol.

Preferably, the invention relates to the use of an extract obtained from a tunicate as biomass for the production of an alcohol. Preferably, the invention relates to a method for producing an alcohol from a tunicate wherein said method comprises:

(i) extracting one or more polysaccharides from said tunicate and subjecting said one or more polysaccharides to enzymatic or acid hydrolysis to form a hydrolysate containing one or more monosaccharides; and (ii) fermenting said one or more monosaccharides to form an alcohol.

The tunicate can be in the form of the whole of the body of the tunicate or it can be in the form of part of the body of a tunicate, preferably the tunic which has been isolated from the rest of the tunicate body. The tunicate can, for example, be freshly harvested or thawed out from a frozen supply. Preferably the tunicate is washed to remove sea salts. Preferably this washing is carried out on wet tunicate, i.e. tunicate that has not been subjected to drying and preferably the washing is carried out with deionised or fresh water.

Before subjecting the tunicate to enzymatic or acid hydrolysis, the tunicate is preferably dried. Preferably, the invention relates to a method for producing an alcohol from a tunicate wherein said method comprises:

(i) drying said tunicate;

(ii) extracting one or more polysaccharides from said tunicate and subjecting said one or more polysaccharides to enzymatic or acid hydrolysis to form a hydrolysate containing one or more monosaccharides; and (iii) fermenting said one or more monosaccharides to form an alcohol.

Drying can be carried out by any means known in the art. Preferably the tunicate is dried to a dryness content (also referred to herein as dryness) of above 50%, more preferably to above 70%, more preferably to above 80%, more preferably to above 85% and even more preferably to above 90%. The tunicate can be dried by pressing it to remove some of the water, laying it on a heated floor to dry it to, for example, about 39% dryness. Then the tunicate can be transferred to an oven, for example, heated to 130-150° C., where it is dried to, for example, about 89% dryness. Alternatively, the tunicate can be dried by freeze-drying or dried by spray-drying, for example, at temperatures of greater than 100° C. over a time scale in seconds. The use of dried tunicate has the advantage of minimising inhibitive effects on any subsequent enzymatic hydrolysis. In one embodiment, the dried tunicate material can be mechanically broken down, by milling for example.

In this aspect of the invention, one or more polysaccharides are extracted from the tunicate. The method of extraction is not limited and includes any method known to those skilled in the art. Preferably extraction involves treating the dried tunicate so that any lignin-like structures present are broken down, together with separating out the one or more polysaccharides. Preferably said one or more polysaccharides comprises cellulose. The tunicate can be processed into a cellulose-rich pulp by means such as those described in Young-Seok Koo et al, "Preparation and Properties of Chemical Cellulose from Ascidan Tunic and Their Regenerated Cellulose Fibers", Journal of applied Polymer Science, Vol. 85, 1634-1643 (2002). In this reference, the tunicate raw material is dried and reduced to powder using a mill. The powder is treated with an aqueous acid solution ($H_2SO_4$), filtered, washed with acetone and water and dried under vacuum at 75° C. The sample is then treated with an alkaline aqueous solution ($NaOH/Na_2S$) and filtered, washed and dried as before. Finally the sample is treated with a bleaching agent (aqueous NaOCl solution) and filtered, washed and dried as before. The resultant sample is rich in cellulose.

In a preferred embodiment of this aspect of the invention, cellulose is extracted from the tunicate by subjecting the tunicate to a drying step, an acid treatment step, an alkali treatment step and an oxidation/bleaching step. The three steps of acid treatment step, alkali treatment step and oxidation/bleaching steps constitute a treatment regime which facilitates the extraction of cellulose from the dried tunicate, for example, by breaking down any lignin-like structures present. After this treatment regime, the solid polysaccharide product can be separated out by filtration or centrifugation. The polysaccharide product can then be washed and dried. The drying step is as described above. The acid treatment step, alkali treatment step and oxidation/bleaching step are further described below.

The acid treatment step is an acid hydrolysis step. The dried sample is treated with an aqueous acid solution, for example, 0.9 wt % $H_2SO_4$ at 180° C. for 2 hours. The resulting product is filtered, washed and dried, for example, at 50° C.

The alkali treatment step is an alkaline hydrolysis/kraft pulping step. The product from the acid treatment step is treated with an aqueous alkali solution, for example, 9/3 wt % NaOH/Na$_2$S solution at 180° C. for 2 hours. The resulting product is filtered, washed and dried, for example, at 50° C.

The oxidation/bleaching step involves treating the product from the alkali treatment step with a bleaching agent, for example 2.9 wt % NaOCl solution at 75° C. for 1 hour. The resulting product is filtered, washed and dried, for example, at 50° C.

The outcome is an extract from a tunicate that is cellulose-rich. This extract can then be subjected to enzymatic or acid hydrolysis to form a hydrolysate containing one or more monosaccharides. This is followed by fermentation of the hydrolysate to produce an alcohol. The steps of enzymatic and acid hydrolysis followed by fermentation and recovery of the alcohol that can be utilised in this aspect of the invention are as previously described. In one embodiment, the method of the invention involves acid hydrolysis of the one or more polysaccharides extracted from the tunicate. Preferably sulphuric acid is used. In one embodiment, the method of the invention involves enzymatic hydrolysis of the one or more polysaccharides extracted from the tunicate. One or more enzymes can be used including enzymes for converting polysaccharides into monosaccharides. Preferably the one or more enzymes convert the cellulose into glucose, for example cellulase and glucosidase.

The invention further provides for a method of producing an alcohol from a tunicate or an extract obtained from a tunicate as described herein which method also comprises a method of farming said tunicate, wherein said tunicate is an ascidian. The method of farming includes growing and harvesting said tunicate and can be as described herein.

Biodiesel

In one aspect, the invention relates to the use of a tunicate or extract obtained from a tunicate for the production of biodiesel.

Biodiesel can be produced from lipids using transesterification. The primary component of biodiesel comprises fatty acid alkyl esters, in particular, fatty acid methyl (or ethyl) esters. Typically, in the production of biodiesel, lipids are mixed with potassium or sodium hydroxide and methanol (or ethanol) and the chemical reaction produces the acid methyl (or ethyl) ester and glycerol.

The present studies show that *C. intestinalis* has a 3.2 weight % gross lipids content. Using the three-dimensional farming model mentioned previously, results in a yield of 29,000 l of animal lipids per hectare of ocean surface area in addition to the ethanol. These animal lipids provide a raw material for biodiesel production through either transesterification or alcoholysis[19]. Using estimates from the literature on 100 mm long *C. intestinalis* of 0.6 g (dry weight), and densities of 3000 individuals per m$^2$ on the ocean floor, we will have a biodiesel yield of 0.058 l/m$^2$ (3,000 individuals/m$^2$×0.0006 kg/individual×0.032=0.058 l/m$^2$), or 580 l/hectare. This calculation is based on one harvest. As it is possible to harvest *C. intestinalis* at least twice a year, there is potential for an annual biodiesel yield of at least 1,150 l/hectare of ocean floor (2 harvests per year×580 l/hectare). However, this calculation is made for 2-dimensional farming, e.g. on the ocean floor. Because ascidians can be farmed in three dimensions in the ocean water column, the potential biodiesel yield per hectare of ocean floor/ocean surface is much greater. Taking a situation where ascidians are grown on in submerged rods that are 20 m in length and 0.4 m in diameter (giving a surface area of 25.12 m$^2$ per rod) and which are spaced 1 m apart throughout 1 hectare (i.e. 10,000 rods). This provides 251,200 m$^2$ of surface area for ascidian growth per hectare of ocean surface. This, based on the above calculations, in turn, could yield an annual production of about 29,000 l of biodiesel per hectare of ocean surface area.

The present studies have shown that this yield can be much greater than the above estimate. The present studies have shown that *C. intestinalis* can grow to about 31 g (1.37 g dry weight) after 6 months of deployment. Further, using elongated members which support a plurality of colonisation surfaces in the form of plates as described herein, densities of 9690 individuals per m$^2$ can be attained. In a 3-dimensional farming model, assuming 3 plates per meter of length on a 20 meter rope and a plate surface area of 0.2 m$^2$, there will be a surface area of 12 m$^2$ per elongated member in the sea, or 120,000 m$^2$ per hectare if the elongated members are spaced 1 m apart. Assuming 2 harvests per year, the annual biodiesel yield per hectare is ca 102,000 l using the same calculation as above (9690 individuals/m$^2$×0.00137 kg×0.032 lipids×120,000 m$^2$×2 harvests per year=102,000 l of biodiesel).

Preferably the invention relates to the use of a tunicate as biomass for the production of biodiesel. In one aspect, the invention relates to a method of producing biodiesel from a tunicate wherein said method comprises subjecting said tunicate to transesterification or alcoholysis. In this method, lipids present in the tunicate are converted into biodiesel by the transesterification or alcoholysis. In this aspect of the invention, the tunicate itself is subjected to transesterification or alcoholysis and no extraction of lipids/fatty acids from the tunicate is necessary.

The tunicate can be in the form of the whole of the body of the tunicate or it can be in the form of part of the body of a tunicate, such as the tunic which has been isolated from the rest of the tunicate body. The tunicate can, for example, be freshly harvested or thawed out from a frozen supply. Preferably the tunicate is washed to remove sea salts. Preferably this washing is carried out on wet tunicate, i.e. tunicate that has not be subjected to drying and preferably the washing is carried out with deionised or fresh water. This advantageously reduces the ash content of the resultant tunicate material.

Before subjecting the tunicate to transesterification, the tunicate is preferably dried. Preferably, the invention relates to a method for producing biodiesel from a tunicate wherein said method comprises the steps of drying said tunicate and subjecting said dried tunicate to transesterification or alcoholysis.

Drying can be carried out by any means known in the art. Preferably the tunicate is dried to a dryness content (also referred to herein as dryness) of above 50%, more preferably to above 70%, more preferably to above 80%, more preferably to above 85% and even more preferably to above 90%. The tunicate can be dried by pressing it to remove some of the water, laying it on a heated floor to dry it to, for example, about 39% dryness. Then the tunicate can be transferred to an oven, for example, heated to 130-150° C., where it is dried to, for example, about 89% dryness. Alternatively, the tunicate can be dried by freeze-drying or dried by spray-drying, for example, at temperatures of greater than 100° C. over a time scale in seconds. The use of dried tunicate has the advantage of minimising inhibitive effects that water has on the transesterification reaction. In one embodiment, the dried tunicate material can be mechanically broken down, by milling for example.

Tunicates comprise naturally occurring lipids and/or fatty acids. The lipids which occur naturally in tunicates include fatty acids and their derivatives (including monoglycerides, diglycerides, triglycerides (also known as fats)), sterols, phospholipids and sphingolipids. In addition, tunicate also comprise fatty acids. The present studies have shown that *C. intestinalis* contains the fatty acid composition shown in FIG. 1. Fatty acids are identified herein by a first number that indicates the number of carbon atoms and a second number that is the number of double bonds. The n3 symbol indicates that the fatty acid is an omega-3 fatty acid which is an unsaturated fatty acid with the third bond from the methyl end of the fatty acid being a double bond. Without limitation, fatty acids isolated from tunicates can comprise one or more of the following fatty acids: 14:0, 16:0, 16:1, 18:0, 18:1, 18:4, 20:0, 20:1, 20:5-n3 (eicosapentaenoic acid); 21:5-n3; 22:6-n3 (docosahexaenoic acid); and 22:5-n3. Without limitation, fatty acids isolated from tunicates can comprise one or more of the following fatty acids: 16:0, 16:1, 16:2, 18:0, 18:1, 18:2, 18:3, 18:4, 20:0, 20:1, 20:2, 20:3, 20:5-n3 (eicosapentaenoic acid); [21:5-n3]; and 22:6-n3 (docosahexaenoic acid). Without limitation, fatty acids isolated from tunicates can comprise one or more of the following fatty acids: 14:0, 16:0, 16:1, 16:2, 18:0, 18:1, 18:2, 18:3, 18:4, 20:0, 20:1, 20:2, 20:3, 20:5-n3 (eicosapentaenoic acid); 21:5-n3; 22:6-n3 (docosahexaenoic acid); and 22:5-n3. Furthermore the present studies show that *C. intestinalis* contains very little to no glycerol. This can be seen in the HNMR results given in FIG. 2. This is particularly advantageous as glycerol is a byproduct in the process for making biodiesel and has to be removed.

In the method of the invention, the tunicate lipids are converted into biodiesel by transesterification or alcoholysis. Transesterification is the general term used to describe the class of organic reactions where an ester is transformed into another ester through interchange of the alkoxy moiety. Tunicate lipids include esters such as mono-, di- and triglycerides. When these are transesterified by reaction with an alcohol then the transesterification process is also known as alcoholysis. Tunicate lipids also contain free fatty acids. When a fatty acid is reacted with an alcohol this process is called alcoholysis.

In the transesterification of fats or triglycerides, the triglyceride reacts with an alcohol in the presence of a strong acid or base to produce a mixture of fatty acid alkyl esters and glycerol. Typically, the alcohol is a monohydric alcohol chosen from methanol, ethanol, propanol or butanol. Typically, the base catalyst is NaOH or KOH. Typically, the acid catalyst is concentrated sulphuric acid. For biodiesel production, base-catalysed transesterification of triglycerides is more commonly used as it proceeds faster than the acid-catalysed transesterification.

The present studies have shown that tunicates can have a high content of free fatty acids. Free fatty acids, when present, can cause a problem in base-catalysed transesterification by reacting with the inorganic base catalyst thus neutralising the catalyst and forming soap. To avoid this happening acid-catalysed transesterification can be used such as described in Gemma Vicente et al., "Direct Transformation of Fungal Biomass from Submerged Cultures into Biodiesel. Energy Fuels", 2010, 24: 3173-3178; and Freeman B, Pryde E H, et al., "Variable affecting the yields of fatty acid esters from transesterificated vegetable oils", JAOCS. 1984, 61(1): 1683-1687.

In one embodiment, a two stage transesterification process can be used. This can involve a first stage where the tunicate lipids are reacted with an alcohol in the presence of a base catalyst, for example, they are reacted with methanol in the presence of KOH, followed by a second stage where the lipids are reacted with an alcohol but in the presence of an acidic catalyst, for example, they are reacted with methanol in the presence of $BF_3$.

The amount of fatty acids present can be ascertained by titration of a sample of the lipids mixture with a standard base solution. In the case of a large amount of free fatty acids in the tunicate lipids, the tunicate (or tunicate lipids/fatty acids) can be subjected to a two stage process involving an esterification process as a first stage which is carried out prior to the transesterification process which is the second stage. In the first stage esterification process, the free fatty acids are esterified with the alcohol in the presence of an acid catalyst such as concentrated $H_2SO_4$. The reaction product contains a lipid phase containing the newly formed fatty acid esters and a glycerol phase. The glycerol phase can be removed and the lipid phase subjected to the second stage transesterification such as described above. Typical two-stage processes are described in Zullaikah S, Lai C C, Vali S R, et al. "A two-step acid-catalyzed process for the production of biodiesel from rice bran oil", Bioresource Technology, 2005, (96): 1889-1896, in Ghadge S V, Raheman H., "Biodiesel production from mahua (*Madhuca indica*) oil having high free fatty acids", Biomass and Bioenergy, 2005, (28): 601-605 and in Chen S, Jian G J, Nie X, Chang X, "Study on Preparation of Biodiesel from Waste Acidificated Oil of High-acid-value", Chemistry and industry of forest products, 2009, 29(4): 47-52.

An alternative process is a simultaneous esterification of free fatty acids and transesterification of triglycerides using enzyme catalyst such as a lipase. Such a process is described in Li N W, Zong M H, Wu H., "Highly efficient transformation of waste oil to biodiesel by immobilized lipase from *Penicillium expansum*", Process Biochemistry, 2009, 44: 685-688.

An alternative process is supercritical methanol transesterification which does not require a catalyst and thus eliminates the problem with soap being formed from free fatty acids. Such a process is described in Demirbas A, "Biodiesel production from vegetable oils via catalytic and non-catalytic supercritical methanol transesterification methods", Progress in Energy and Combustion Science, 2005, 31: 466-487

The transesterification or alcoholysis can be carried out by means known in the art such as described in WO 2009089802.

Preferably, when obtained as fresh lipids from fresh tunicates, the preferred method is alkali-catalysed transesterification. When the acid value is high, for example, for lipids obtained from long-stored samples of tunicates, acid catalysed alcoholysis or a two step (stage) method as described above is preferred.

Preferably the biodiesel is recovered from the transesterification or alcoholysis reaction mixture. The products biodiesel and glycerol are immiscible. Biodiesel can be recovered from the reaction mixture by a series of centrifugation and separation (to remove the tunicate residue), evaporation and solvent extraction steps.

Preferably, the invention relates to the use of an extract obtained from a tunicate as a biomass for the production of biodiesel. In one aspect, the invention relates to a method for producing biodiesel from a tunicate wherein said method comprises:
  (i) extracting lipids/fatty acids from said tunicate and
  (ii) converting said lipids/fatty acids into biodiesel by transesterification or alcoholysis.

In a preferred embodiment this aspect of the invention relates to a method of producing fatty acid alkyl esters. Preferably the fatty acid alkyl esters are methyl or ethyl esters.

The tunicate can be in the form of the whole of the body of the tunicate or it can be in the form of part of the body of a tunicate, such as the tunic which has been isolated from the rest of the tunicate body. The tunicate can, for example, be freshly harvested or thawed out from a frozen supply. Preferably the tunicate is washed to remove sea salts. Preferably this washing is carried out on wet tunicate, i.e. tunicate that has not be subjected to drying and preferably the washing is carried out with deionised or fresh water.

In the method of the invention the extraction of lipids/fatty acids from the tunicate can be carried out by means known in the art such as filtration-centrifugation, solvent extraction, acid extraction, pressing and distillation. Preferably solvent extraction is used and preferably it is performed using diethyl ether or petroleum ether. Preferably Soxhlet extraction is used.

Preferably Soxhlet extraction using petroleum ether is used. After a Soxhlet extraction step, the resultant product can be filtered to separate the filtrate from the tunicate residue and the filtrate then evaporated to yield the lipids/fatty acids.

Before the step of extracting the lipids/fatty acids from the tunicate, preferably the tunicate is dried. In one aspect, the invention relates to a method for producing biodiesel from a tunicate wherein said method comprises:
  (i) drying the tunicate;
  (ii) extracting lipids/fatty acids from said dried tunicate and
  (iii) converting said lipids/fatty acids into biodiesel by transesterification or alcoholysis.

Drying can be carried out as previously described.

In the method of the invention, the extracted lipids/fatty acids are converted into biodiesel by transesterification or alcoholysis. The transesterification or alcoholysis of the lipids/fatty acids can be carried out as described above.

Preferably the biodiesel is recovered from the transesterification or alcoholysis reaction mixture. Biodiesel can be recovered from the reaction mixture by a series of separation, evaporation and solvent extraction steps.

In use, the biodiesel can be used alone or blended with mineral diesel, for example in amounts of up to 15% biodiesel blended with mineral diesel.

The invention further provides for a method of producing biodiesel from a tunicate or an extract obtained from a tunicate as described herein which method also comprises a method of farming said tunicate, wherein said tunicate is an ascidian. The method of farming includes growing and harvesting said tunicate and can be as described herein.

Integrated Method

In one aspect, the invention relates to use of a tunicate for the production of more than one biofuel selected from an alcohol and biodiesel. Specifically the invention provides a method of producing a first biofuel from a tunicate according to one of the aforementioned methods and additionally producing a second biofuel from said tunicate wherein the first and second biofuels are different and are selected from an alcohol and biodiesel.

In one embodiment, the invention provides a method for producing an alcohol from a tunicate according to the method described above which method further comprises producing biodiesel from said tunicate according to one of the methods described above.

In this aspect of the invention, preferably the tunicate is first dried. Drying can be carried out as previously described. Then the one or more polysaccharides and fatty acids/lipids are extracted from said tunicate and used to produce the relevant biofuels in the methods described above.

In one embodiment, the method involves:
  (i) drying the tunicate
  (ii) extracting one or more polysaccharides from said dried tunicate and subjecting said one or more polysaccharides to enzymatic or acid hydrolysis to form a hydrolysate containing one or more monosaccharides;
  (iii) fermenting said one or more monosaccharides to form an alcohol;

wherein during step (ii) or step (iii), at least one solution is formed which contains lipids/fatty acids and the method further involves extracting said lipids/fatty acids from said solution and converting said lipids/fatty acids into biodiesel by transesterification or alcoholysis. The solution can be formed (a) during the step of extracting one or more polysaccharides from said dried tunicate and/or (b) during the step of subjecting said one or more polysaccharides to enzymatic or acid hydrolysis to form a hydrolysate containing one or more monosaccharides, and/or (c) during or after the fermentation step. In (a) the solution can be that formed during the treatment of the dried tunicate to enrich the cellulose or C6 sugar content in the residue. In (b) the solution can be the hydrolysate. In (c) the solution can be the fermentation broth. The lipids/fatty acids will form a floating layer in said solutions with or without the assistance of addition of an organic solvent lighter than water. The lipids/fatty acids can be recovered by means known in the art.

In another embodiment, the method involves:
  (i) drying the tunicate
  (ii) subjecting said dried tunicate to enzymatic or acid hydrolysis to form a hydrolysate containing one or more monosaccharides;
  (iii) fermenting said one or more monosaccharides to form an alcohol;

wherein during step (ii) or (iii), at least one solution is formed which contains lipids/fatty acids and the method further involves extracting said lipids/fatty acids from said solution and converting said lipids/fatty acids into biodiesel by transesterification or alcoholysis. The solution can be the hydrolysate or the fermentation broth. The lipids/fatty acids will form a floating layer in said solutions and can be recovered by means known in the art.

In another embodiment, the method involves:
  (i) drying the tunicate;
  (ii) extracting lipids/fatty acids from said dried tunicate;
  (iii) converting said lipids/fatty acids into biodiesel by transesterification or alcoholysis;

wherein during the step of extracting the lipids/fatty acid from said tunicate, tunicate residue is formed and the method further involves extracting one or more polysaccharides from said tunicate residue, subjecting said one or more polysaccharides to enzymatic or acid hydrolysis to form a hydrolysate containing one or more monosaccharides and fermenting said one or more monosaccharides to form an alcohol.

In another embodiment, the method involves:
  (i) drying the tunicate;
  (ii) subjecting said dried tunicate to transesterification or alcoholysis thereby converting lipids/fatty acids present in said dried tunicate into biodiesel;
  (iii) recovering the biodiesel;

wherein during the step of recovering the biodiesel from said dried tunicate, tunicate residue is formed and the method further involves extracting one or more polysaccharides from said tunicate residue, subjecting said one or more polysaccharides to enzymatic or acid hydrolysis to form a hydrolysate containing one or more monosaccharides and fermenting said one or more monosaccharides to form an alcohol.

In the embodiments described above for the integrated method aspect of the invention, the drying step may be omitted.

The methods of extracting one or more polysaccharides, enzymatic or acid hydrolysis, fermentation, extracting lipids/fatty acids, transesterification or alcoholysis, recovery of the alcohol and/or biodiesel are known in the art or are as described previously.

This aspect of the invention has a clear advantage in that it results in increased biofuel output per unit weight of tunicate biomass and further that it increases the ocean area based production of biofuel.

Industrial Scale-Up

The methods of the present invention are suitable for industrial scale-up. For the methods of producing alcohol disclosed herein, existing reactors used in the pulp or paper industry could be used, for example. For the methods of producing biodiesel disclosed herein, existing reactors for producing biodiesel from vegetable oil could be used, for example.

3-Dimensional Farming

This aspect of the invention relates to a method of 3-dimensional farming of ascidians in the sea. The object is to provide a method of farming which enables the production of large quantities of ascidians. Another object is to provide a method of farming which favours the natural recruitment and settlement of ascidians and does not involve a step whereby the ascidian population has to be seeded or supplied from nursery stock. Another object is to provide a method of farming which results in the growth of a monoculture of ascidians with minimal biofouling caused by colonisation of organisms other than ascidians. Each of the embodiments of the 3-dimensional farming methods described herein meets at least one of these objectives.

In one aspect, the invention relates to a method of 3-dimensional farming of ascidians in the sea.

In this aspect, the invention relates to a method for farming ascidians comprising the steps of:

(a) colonising surfaces of a sub-sea structure with ascidians; and
(b) harvesting said ascidians from said structure, wherein said structure comprises a plurality of elongate members having colonisation surfaces and said structure defines a three-dimensional sub-sea region arranged to support ascidian colonisation.

Preferably, the colonising of the surfaces of the sub-sea structure is achieved by natural recruitment and settlement of ascidians.

As used herein, an elongate member can be a rope (FIG. 3), rod or hollow cylinder. Preferably the rope, rod or hollow cylinder has a diameter of 1 to 10 cm, more preferably a diameter of 2 to 4 cm, even more preferably 2 cm.

In one embodiment the colonisation surfaces comprise the surfaces of the rope, rod or hollow cylinder. In this embodiment, the sub-sea structure comprises a plurality of elongate members chosen from ropes, rods or hollow cylinders or combinations thereof. The ascidians colonise the surfaces of the elongate members and, are harvested therefrom. In this embodiment, preferably, the plurality of elongate members comprises at least one hollow cylinder which, preferably, has a diameter of greater than 10 cm, more preferably greater than 20 cm, and even more preferably between 30 and 70 cm.

In one embodiment, the elongate member has a support function. In this embodiment the elongate member can be referred to as an elongate support member and is provided with a plurality of colonisation members wherein each colonisation member is coupled to said support member. Each colonisation member comprises at least one colonisation surface. Preferably the colonisation surface is substantially smooth and uninterrupted.

In one embodiment, at least one of the colonisation surfaces is planar. Preferably, this surface is vertical or horizontal. In this context, the terms vertical and horizontal are in relation to the elongate member (or elongate support member). More preferably, this surface is planar and horizontal. The present studies show that such a surface favours the dominance of ascidians (reduced biofouling).

In one embodiment, at least one of the colonisation members having a planar surface is in the form of plate or disc. Preferably they are discs of about 0.4-0.6 m in diameter and, in one embodiment, placed at a distance of 1-3 m apart on the elongate member. In another embodiment, the discs are placed at a distance of 0.2-1 m apart on the elongate member, preferably 0.3-0.5 m apart. These can be attached to the elongate member by means known in the art. The colonisation surfaces or members can be plates which are square or rectangular in shape. These can be about 0.2-1.5 m in either width or length. Preferably they are about 0.2-0.6 m in either width or length, more preferably they are about 0.4-0.6 m in either width or length. In one embodiment, these are placed at distances of 1-3 m apart on the elongate member. In another embodiment, they are placed at distances of 0.2-1 m apart on the elongate member, preferably 0.3-0.5 m apart. These can be attached to the elongate member by means known in the art.

In one embodiment at least one of the colonisation members is in the form of a cylinder or a hollow tube. Preferably they are hollow tubes of about 0.4-0.6 m in diameter. These can be coupled to the elongate member by means known in the art. In one embodiment, they are attached to the elongate member by fastening means positioned at either end or both ends of the cylinder.

If needed, the colonisation members can be coupled to more than one elongate member.

The colonisation members are preferably sited along the elongate support member at least 20 cm apart, preferably they are between 25 cm and 1 m apart. In the case where the colonisation members have horizontal planar surfaces, this distance is required to enable sufficient growth of the ascidians.

Preferably the colonisation member is perforated or made of a perforate material or mesh. This reduces the cost of the colonisation member and also aids access of ascidian larvae between upper and lower or inner and outer colonisation surfaces.

In one embodiment an elongate member supports a plurality of generally radially extending colonisation surfaces or members.

Figure 4:
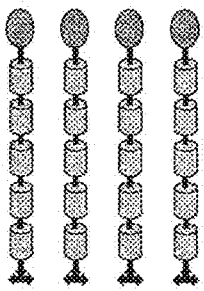
FIG. 4 is another embodiment of an elongate member which comprises hollow plastic PVC tubes attached to a surface long-line system, using a buoy and a weight to keep the rope vertical in the water column.

The generally radially extending colonisation surfaces or members can be cylinder-shaped or hollow tubes (FIG. 4). Preferably they are hollow tubes of about 0.4-0.6 m in diameter. These can be attached to the elongate member by means known in the art. In one embodiment they are attached to the elongate member by fastening means positioned at either end or both ends of the cylinder.

Figure 5:
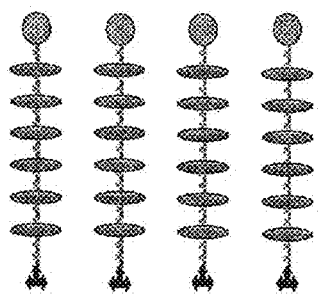
FIG. 5 is another embodiment of an elongate member which comprises PVC discs attached to a surface long-line system, using a buoy and a weight to keep the rope vertical in the water column.
Figure 6:
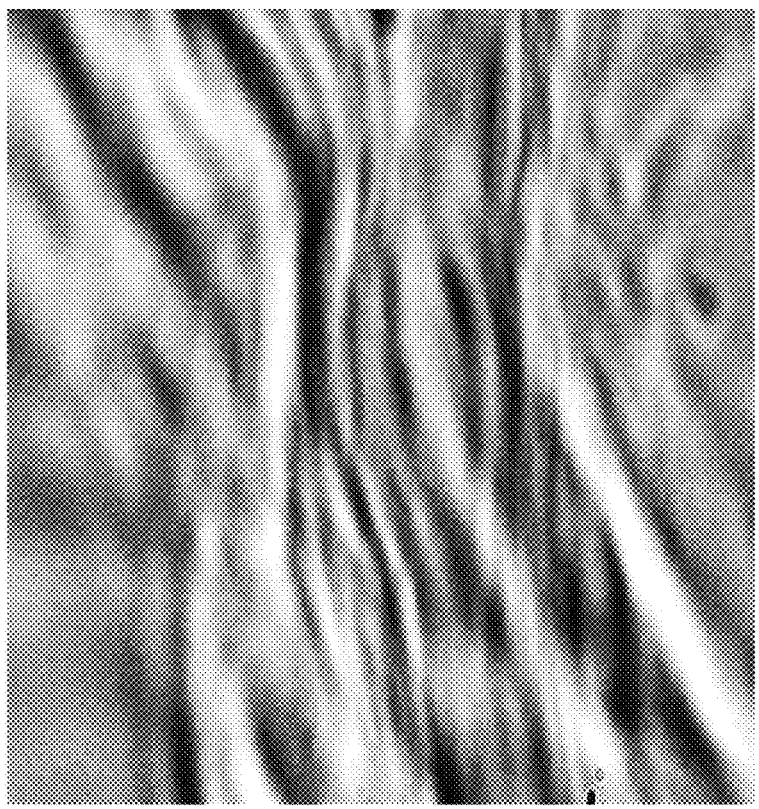
FIG. 6(ii) is a photograph of cellulose obtained from a wood sample as described in the examples, under microscopy (×40).
Figure 6:
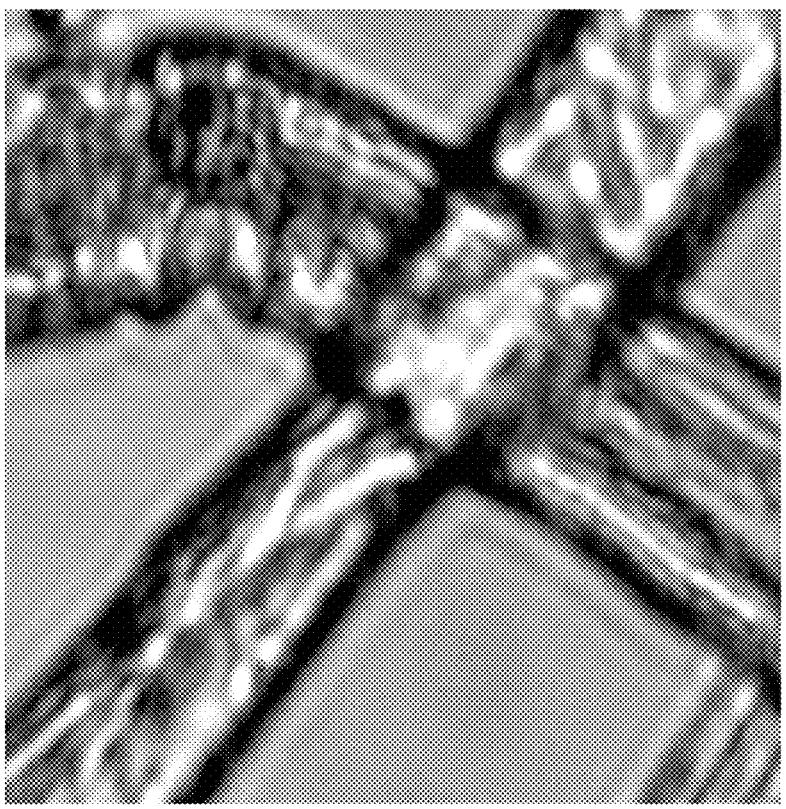

The generally radially extending colonisation surfaces or members can be disc-shaped (FIG. 5). Preferably they are discs of about 0.4-0.6 m in diameter and, in one embodiment, placed at a distance of 1-3 m apart on the elongate member. In another embodiment, the discs are placed at a distance of 0.2-1 m apart on the elongate member, preferably 0.3-0.5 m apart. These can be attached to the elongate member by means known in the art.

The generally radially extending colonisation surfaces or members can be rectangular in shape. Preferably they are about 0.2-0.6 m in either width or length, more preferably they are about 0.4-0.6 m in either width or length. In one embodiment, these are placed at distances of 1-3 m apart on the elongate member. In another embodiment, they are placed at distances of 0.2-1 m apart on the elongate member, preferably 0.3-0.5 m apart. These can be attached to the elongate member by means known in the art.

Figure 2:
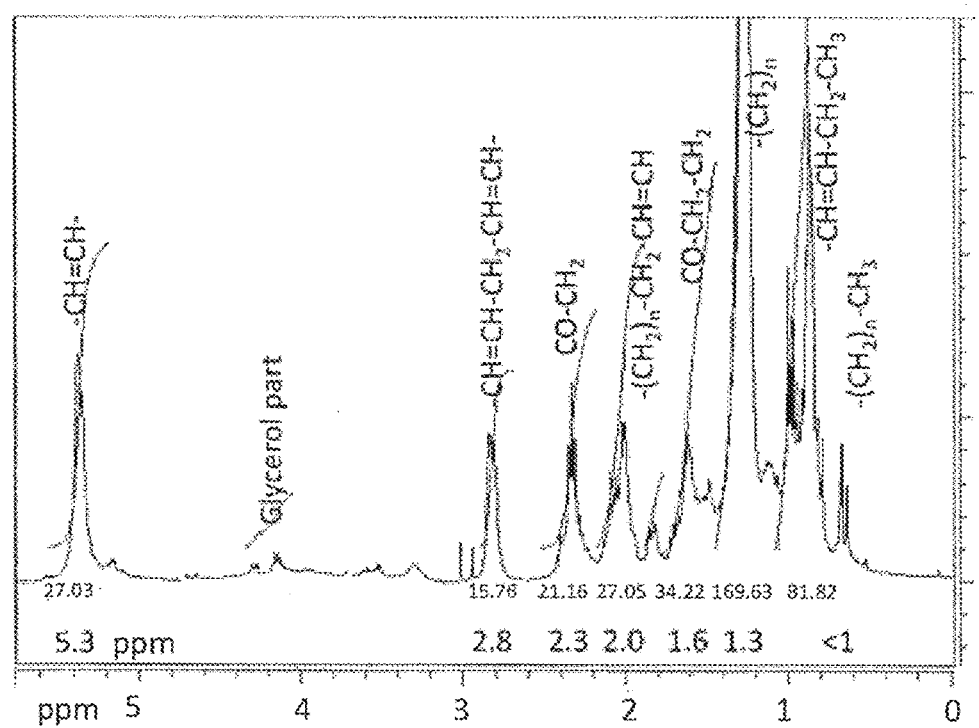
FIG. 2 is a HNMR analysis of lipids extracted from a *C. intestinalis* sample.
Figure 3:
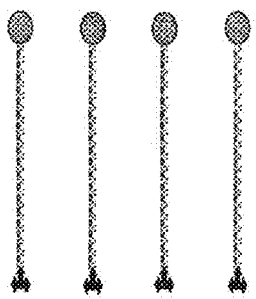
FIG. 3 is an embodiment of an elongate member which is a rope attached to a surface long-line system, using a buoy and a weight to keep the rope vertical in the water column.

In use, the elongate members can be attached to a surface long-line system, using a buoy and a weight to keep the elongate member vertical in the water (FIGS. 2, 3 and 4).

A sub-sea structure or apparatus used to colonise the tunicates will now be described with reference to FIG. 7 and examples A to E.

Figure 7:
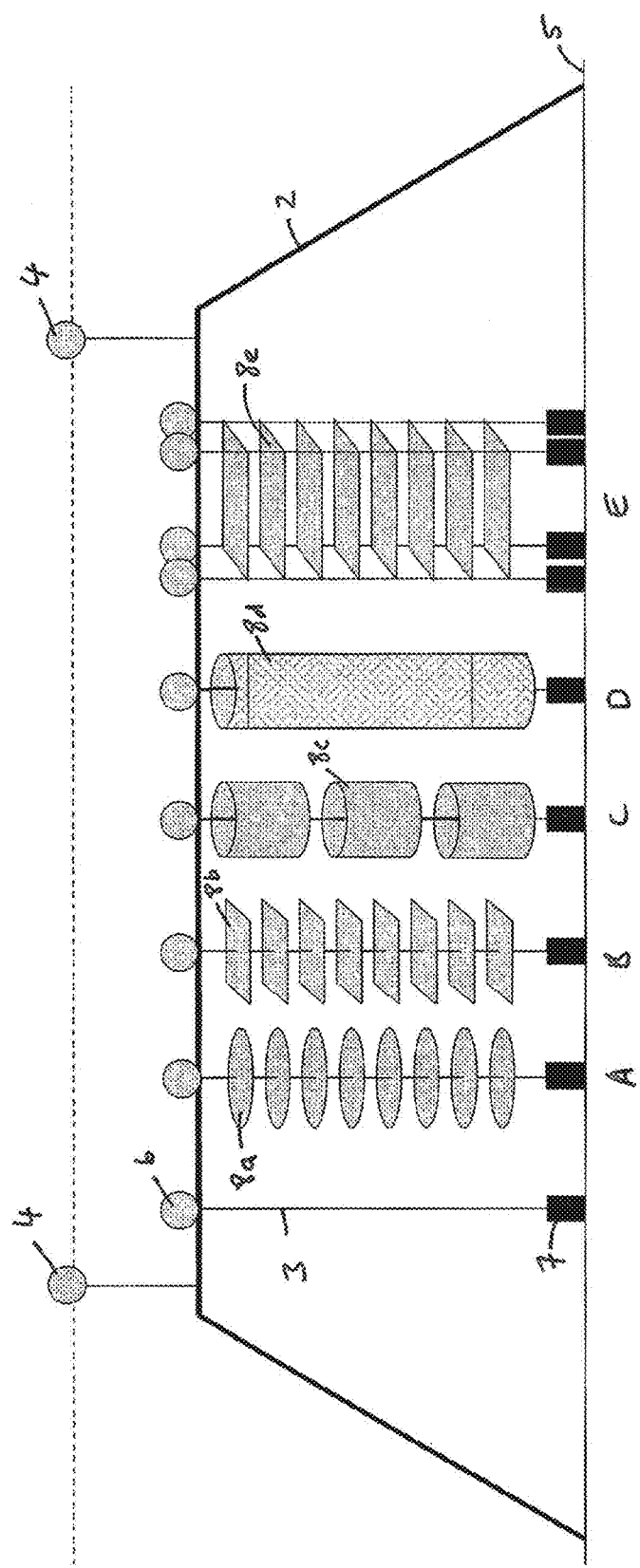
FIG. 7 illustrates a number of alternative arrangements of colonisation apparatus.

FIG. 7 illustrates a long-line system (1) for colonisation of tunicates. The long-line system (1) consists of a number of elongate members (3) coupled to a long-line (2). The long-line itself is attached to at least one sea level buoy (4) along the central portion of the long-line (2) in order to keep it in the correct orientation in the water. The ends of the long-line (2) are attached to sea bed (5).

A buoy (6) is also attached to one end of each of the elongate members (3) and a weight (7) is attached to the other end in order to keep the elongate members (3) vertical in the water.

As illustrated in FIG. 7, a variety of different structures of elongate member (3) may be used in combination with the long-line (2).

As shown in each example the elongate members (3) comprise a plurality of colonisation members (8) in a stack or array formation.

The colonisation members (8) may have a variety of shapes including planar or prism. Colonisation members (8) including at least one planar colonisation surface may be favoured over other shapes since the planar surface facilitates colonisation and harvesting as discussed below.

The elongate members (3) shown in examples A and B include a plurality of planar colonisation members (8a-8e). The elongate member (3) is coupled to the colonisation members (8) through the centre of the colonisation member (8) (a disc in example A and a square in example B) using a suitable coupling arrangement.

The colonisation members (8) themselves each have at least one uninterrupted surface i.e. a surface without any substantive ridges, projections or the like extending from the surface which would be detrimental to tunicate colonisation. Further, such a surface discourages biofouling caused by the settlement of organisms other than the ascidians.

Examples C and D are cylindrical and have one uninterrupted surface, the circumferential external surface which forms the cylinder. In one embodiment, the cylinder is open at both ends and the circumferential internal surface which forms the cylinder is also an uninterrupted surface. In one embodiment, the colonisation member is a cylinder with one or both ends covered forming upper and/or lower planar surfaces. In this embodiment, the cylinder has three uninterrupted surfaces i.e. an upper and lower surface and a circumferential surface forming the cylinder.

Examples A, B and E each have two planar surfaces per colonisation member (8) (an upper and an underside surface).

The planar surfaces of the colonisation members (8a and 8b) provide an uninterrupted surface extending circumferentially and radially around the coupling of the elongate member (3) to the colonisation member (8). Thus, access to the surface is unrestricted allowing tunicates to easily colonise the surface. Additionally this access facilitates harvesting of tunicates from the colonisation member (8). Examples C and D comprise the circumferential external surface which is similarly uninterrupted again allowing colonisation and harvesting.

The colonisation members (8) may be any suitable shape such as a circular disc (8a) as shown in example A. The colonisation members (8) may also be square or rectangular shape (8b) as shown in example B.

The elongate member (3) of example C includes a plurality of cylindrically shaped colonisation members (8c). The cylindrically shaped colonisation members (8c) are coupled to the elongate member (3) through the central axis of each cylinder. In one embodiment, each cylindrically shaped colonisation member (8c) can comprise three colonisation surfaces, including two planar colonisation surfaces being the end faces of each cylinder. Thus three uninterrupted colonisation surfaces are provided. The colonisation members (8) are not limited to cylindrically shaped colonisation members and may be formed of any prism.

The elongate member of example D includes a single cylindrically shaped colonisation member (8d). The colonisation member (8d) is coupled to the elongate member (3) through the central axis of the cylinder. The single cylindrically shaped colonisation member is open at both ends. The colonisation member (8d) is perforated or formed of a mesh. This aids access of ascidian larvae to the inner surface of the cylinder, thus promoting settlement of ascidians on the inner surface. However more than one colonisation member (8) could be provided made of a perforate material or mesh. In one embodiment, three uninterrupted colonisation surfaces can be provided, including two planar colonisation surfaces being the end faces of each cylinder.

The embodiment of example D could also be considered an elongate member which is a hollow cylinder and which, preferably, has a diameter of greater than 10 cm, more preferably greater than 20 cm, and even more preferably between 30 and 70 cm.

The elongate member of example E includes a plurality of elongate members (3) and a plurality of colonisation members (8e). Each elongate member (3) is coupled to the edge of each colonisation member (8e). The elongate members (3) are equally spaced around the edge of each colonisation member (8e) in order to maintain the planar shape of the colonisation members (8e). A number of rectangular shaped colonisation members (8e) are shown in example E. However the shape of the colonisation members (8) may be any shape provided an uninterrupted colonisation surface is provided.

The colonisation members described herein, including the radially extending colonisation surfaces or members are preferably made of plastic, preferably PVC. Preferably they are made of a plastic or plastics material for example acrylic (Perspex), polypropylene, polybutylene, high density polyethylene or PVC.

Preferably the colonisation surfaces are dark in colour, preferably they are darker than white and preferably they do not reflect light. Preferably the colonisation surfaces are black or dark grey. It has been found that by employing colonisation surfaces which have a colour that has a low contrast to the sea, less competitive biofouling occurs.

Preferably the colonisation surface is made of a plastics material, is dark in colour and is a horizontal planar surface. Preferably the colonisation surface is made of a plastics material, is dark in colour and is a horizontal planar surface.

The sub-sea structure defines a three-dimensional sub-sea region arranged to support ascidian colonisation. Preferably the sub-sea structure comprises between 5,000 and 15,000 elongate members. Preferably the elongate members are between 5 and 70 m in length and most preferably the elongate members are between 5 and 50 m in length. In one embodiment the elongate members are between 10 and 70 m in length, in another embodiment they are between 15 and 25 m in length, and in another embodiment, they are 20 m in length. In one embodiment, the elongate members are between 5 to 20 m in length. In one embodiment, the elongate members are between 5 to 10 m in length. Preferably the elongate members are spaced at a distance of 0.5 m to 4 m apart, more preferably 1 to 1.5 m apart. Preferably one sub-sea structure occupies an ocean surface area of between 5,000 m$^2$ to 1,000,000 m$^2$ (100 hectares). Preferably one sub-sea structure occupies an ocean surface area of between 5,000 m$^2$ to 20,000 m$^2$. Preferably one sub-sea structure occupies an ocean surface area of between 10,000 m$^2$ to 1,000,000 m$^2$ (100 hectares). Preferably the sub-sea structure occupies an area of 10,000 m$^2$ (one hectare).

Harvesting can be carried out by scraping the ascidians off the colonisation surfaces or by using vacuum suction. Harvesting can be carried out with the sub sea structure in situ, for example by using a vacuum hose extended from a boat. In situ harvesting can also be carried out by using a remotely operated vehicle (ROV) to harvest the ascidians off the colonisation surfaces. On a smaller scale, harvesting can be carried out, for example, on a boat after the elongate members have been pulled out of the water onto said boat.

Preferably the ascidians are harvested when they are greater than 10 g in weight, more preferably when they are greater than 20 g in (wet) weight, and even more preferably when they are greater than 30 g in weight.

The present studies suggest a growth rate of ascidians of $M=(1\times10^{-13})\times D^{6.41}$, where M is mass in grams and D is time in days. Based on this, a deployment period of 6 months will yield ascidians of about 31 g wet weight (or 1.37 g dry weight). The present studies also show that a continuous recruitment of larva to the sub-sea structure from March to the end of August in temperate to cool waters, and that the ascidians remain on the structures for at least 6 to 9 months. There are therefore two distinct harvesting strategies. The first 5 to 6 months of deployment of the sub-sea structure. The second is a continuous harvesting (10 month) with deployments of the elongated members from March to August and harvesting from August to May. In the latter harvesting strategy, ascidians that have been grown for 5-9 months are harvested which will result in an increase the total biomass yield.

The tunicate farms of the present invention should be placed in the sea. Preferably, but not exclusively, they should be located in nutrient rich waters. The farms can be placed both offshore and in coastal areas. Preferably, but not restricted to, the farms are placed in coastal areas, fjords, bay areas and in estuaries.

Ascidians are known to be efficient filter feeders, i.e. they attain their food by passing water through a feeding filter that retains the food particles freely suspended in the water. In water masses with large input of nutrients from e.g. sewage and agricultural activities (terrestrial and aquaculture), phytoplankton will use this excess nutrient load to form large blooms (i.e. increase their growth rates). This is called eutrophication and as the excess blooms of alga die, the degradation of these particles will reduce the oxygen in the water, leading to a reduction of biodiversity in this ecosystem. Nutrients are bound to phytoplankton, and as the ascidians eat phytoplankton for growing, and as they are removed and used for biofuel, the nutrients are removed from the waters and consequently they will reduce the effect of eutrophication of an ecosystem. Therefore, ascidian farms can advantageously be used for remediation purposes in areas with large nutrient inputs from human activities. Preferably the method of farming of ascidians disclosed herein is also a method of reducing the effect of eutrophication of the sea. Preferably, the method of farming ascidians as disclosed herein involves placing the sub-sea structure in a sea region subject to eutrophication or high nutrient load.

In another aspect of the invention, there is provided a method for producing a biofuel from ascidians as described herein comprising the steps of:

(a) colonising surfaces of a sub-sea structure with ascidians; and (b) harvesting said ascidians from said structure, wherein said structure comprises at least one elongate member supporting a plurality of generally radially extending colonisation surfaces or members.

In one aspect of the invention there is provided a method for producing a biofuel from an ascidian as described above which method comprises a method of farming said ascidian according to the method described above.

Advantages

There are many advantages in using ascidians as a source of biomass for the production of the biofuels as described herein. These include: (i) they have very high growth rates which results in a large annual biomass production; (ii) they are relatively easy to culture and harvest; (iii) they do not require arable land for growth and therefore they do not compete with terrestrial food crops; (iv) they contain significant quantities of $C_6$ sugars (for ethanol) and fatty acids (for biodiesel); (v) the extraction of sugar and oils are easier from biomass derived from ascidians than from wood; (vi) the ascidians will have a remediation effect in eutrophic waters as they are filter feeders and capable of removing large quantities of algae; (vii) they can be harvested in situ in the ocean, a major advantage compared to, for example, genetically modified algae which have to be cultured in bioreactors which are subject to strict regulations regarding handling and waster management; (viii) ascidian culture installations will provide excellent reef possibilities for local fish recruitment; (ix) they are environmentally friendly as they have a low impact on the environment.

The present invention is further described by the following non-limiting examples.

Example 1—Drying of Tunicate

Step 1 Raw Material—Drying

Step 1A 4 kg of fresh sample was obtained by scraping ascidians (*C. intestinalis*) that were settled to a rope attached to a longline system. This raw material was placed in a rectangular PVC basket with a grid at the bottom (W×L×H=22 cm×52 cm×25 cm) having an aluminium frame and legs of 4 cm. The raw material was subjected to pressing by placing a PVC plate on top of the raw material and placing a 12 kg weight on top of the PVC plate. This corresponds to a pressure of 10 g/cm². The raw material was pressed overnight. After this pressing step, the sample weighed 2.65 kg, i.e. 66.2 wt % of the initial wet weight of 4 kg. The sample was then spread between layers of newspaper on a heated floor for approximately 24 hours. The newspaper was renewed 3 to 4 times during this period. This procedure produced a "wet" sample weighing 350 g, i.e. 9 wt % of the initial wet weight of 4 kg. A final drying process was performed using an oven for 30-60 minutes at 130-150° C. and this produced a "dry" sample weighing 175 g, i.e. 4 wt % of the initial wet weight of 4 kg. The "wet" sample had a dryness content of 39% and the "dry" sample had a dryness content of 89%. The dryness content was calculated after drying the sample by infra-red heating at 105° C. until a constant weight is reached and equates to the weight percent of resultant dried material based on the wet weight of the tunicate material prior to drying.

Step 1B

An alternative drying procedure was also employed. This involved the use of 3 Camwear® beakers (Cambro), two 12 l and one 18 l as press/water collector systems. One of the two 12 l beakers had holes drilled in the bottom. 2.8 kg of ascidians were placed in the drilled 12 l beaker and left to drain without pressure for 2 hours. Water was collected in the second 12 l beaker which was situated under the drilled 12 l beaker. 5 l of water were poured into 18 l beaker and this was placed on top of the ascidians in the 12 l beaker for 3-4 hours. To gradually increase the pressure, another 10 l of water were added to the 18 l beaker. This corresponds to a final pressure of 28 g/cm². The ascidians were kept under this pressure overnight. As a result, 1.2 l of water were drained from starting 2.8 kg of raw material. Finally, the sample was dried in an oven at 130-150° C. for 2-3 hours.

Example 2—Compositional Analysis of Tunicate

Step 2 Composition Analysis

The dried sample of step 1A was analysed for:

(i) ash (inorganic compound) content (this was measured by burning and with the use of FTIR (fourier transform infra-red) spectroscopy);

(ii) $CaCO_3$ content (this was measured by $CO_2$ emission after acid treatment);

(iii) lignin content (this was determined by both kappa number by the method set out in Li, J.; Gellerstedt, G., "Kinetics and mechanism of kappa number determination." Nordic Pulp Pap. Res. J. (1998), 13(2), 147-152) and Klason lignin determination by the method of the Tappi standard, T 222 om-02); and (iv) lipids content and fatty acid composition (this was determined by the standard method described in Association of Official Analytical Chemists (AOAC) method 983.23 and European Pharmacopoeia "2.4.22. Composition of fatty acids by gas chromatography")

The results were:

Ash: 47 wt % (therefore 53 wt % of the sample is composed of organic compounds), mainly silicates.

$CaCO_3$: ~1.6 wt %

Lignin like substances: 6.3 wt % (kappa number) and 7.2 wt % (klason lignin)

Lipids content: 1.7-3.2%

Fatty acid composition: see FIG. 1.

Example 3—Extraction of Cellulose from Tunicates

Step 3 Preparation of Cellulose Microfibrils

Cellulose microfibrils were prepared from a dried sample of the raw material as obtained in step 1A. The dried sample was subjected to acid hydrolysis followed by alkaline hydrolysis/Kraft pulping, followed by oxidation and bleaching.

Acid hydrolysis: 20 g of dried sample was added into 200 ml of 0.9 wt % $H_2SO_4$ and heated to 180° C. for 2 hours. The remaining residue was filtered out and washed and dried at 50° C.

Alkaline hydrolysis/Kraft pulping: The dried product obtained above was added into 100 ml of 9/3 wt % NaOH/$Na_2S$ solution and heated to 180° C. for 2 hours. The remaining residue was filtered out and washed and then dried at 50° C.

Oxidation and bleaching: The dried product after the alkaline treatment above was added into 100 ml of 2.9 wt % NaOCl solution and heated to 75° C. for 1 hour followed by filtration, washing and drying at 50° C. Pure cellulose was obtained (FIG. 5(i)) at a yield of 3.6 wt % based on weight of the starting material, i.e. the dried sample of the raw material obtained in step 1A. Sugar analysis shows that it contains glucose in an amount of greater than 80 wt % as the sole neutral sugar. This was determined according to Tappi standard TAPPI T 249 cm-09 "Carbohydrate composition of Extractive-free Wood and Wood Pulp" modified in that the acid hydrolysis of the cellulose was performed at 120° C. for one hour instead of 100° C. for four hours.

The yield from the acid hydrolysis step was 21 wt % of the dried sample, the yield from the alkaline hydrolysis/Kraft pulping step was 33 wt % (based on the weight of the dried starting sample after the acid hydrolysis) and the yield from the oxidation/bleaching step was 52 wt % (based on the weight of the dried starting sample after the alkaline hydrolysis).

The resultant sample of cellulose micofibrils had a viscosity of 500 dm³/kg, corresponding to a degree of polymerization (DP) of 936 (approximately 150 K Dalton). The sample of cellulose micofibrils had too low a solubility in LiCl/DMAc solution to perform a LiCl/DMAc SEC analysis (an analysis to evaluate the molecular size of a polymer). This suggests that the obtained cellulose has a distinct structural difference from wood cellulose because wood cellulose is commonly soluble in this LiCl/DMAc solution. This was also confirmed by microscopic analysis. Under microscopic analysis, the cellulose microfibrils obtained appear very different to wood cellulose microfibrils, with the former being longer, thicker and more evenly shaped (FIGS. 5(i) and (ii)).

Example 4—Comparison of Hydrolysis Conditions for Cellulose in Tunicates

Step 4 Comparison of Cellulose Hydrolysis Conditions

In this example, a "wet" sample and a "dried" sample of the raw material obtained in step 1 (see above) and a reference sample of pure cellulose (the dissolving pulp obtained from spruce wood) were subjected to both acidic and enzymatic hydrolysis.

A. Acid Hydrolysis

In each case, 1 g of the sample was subjected to acid hydrolysis in 40% $H_2SO_4$ (solid/liquid=1/10) at 90° C. for 1 hour. The resulting hydrolysis yield to glucose on available cellulose was determined according to Tappi standard TAPPI T 249 cm-09 "Carbohydrate composition of Extractive-free Wood and Wood Pulp" without the prehydrolysis of the sample:

| | |
|---|---|
| Reference sample | 3.6 wt % |
| Dried sample | 6.6 wt % |
| Wet sample | The solution of the "wet" sample became very viscous during acid hydrolysis and could not be sampled accurately for a reliable glucose content determination. |

B. Enzymatic Hydrolysis

In each case, 1 g of the sample was subjected to enzymatic hydrolysis (solid/liquid=1/30) using Novozymes 342 (a commercial enzyme product from Novozymes, containing endoglucanase, exoglucanase, and β-glucosidase) at 40° C. for 5 hours at pH 7. The resulting hydrolysis yield to glucose on available cellulose was:

| | |
|---|---|
| Reference sample | 2.0 wt % |
| Dried sample | 1.0 wt % |
| Wet sample | 3.5 wt % |

Although the "wet" sample hydrolysed faster, an inhibitive effect from the "wet" sample to enzymatic hydrolysis was observed. The glucosidase activity was partially hindered and as a result, a substantial amount of cellubiose was detected in the product from the hydrolysis of the "wet" sample. No cellubiose was detected in the product from the hydrolysis of either the reference sample or the dried sample.

Example 6—Biodiesel Production (A) Extraction of Lipids from Tunicate and Transesterification of Extracted Lipids
(i) Extraction of Lipids from Dried Tunicate.

A sample of tunicate was freeze-dried. 106 grams of the dried tunicate was subjected to extraction in Soxhlet equipment using 800 ml petroleum ether (30-60° C.) for 6 hours. The resultant product was filtered to separate the solution (filtrate) from the solid tunicate material. The filtrate was evaporated under vacuum using a rotary evaporator. 3.2 grams of lipids was obtained (3 wt % yield based on weight of dried tunicate).

(ii) Transesterfication of Extracted Lipids—Base Catalysed 50 mg KOH was added into 20 ml methanol under vigorous stirring. The solution obtained was then added to 1 gram of the lipids obtained in the previous step. The mixture was heated to reflux and kept under reflux for 4 hours. The mixture was then cooled and left to stand. After which, the upper layer was separated out and evaporated under vacuum using a rotary evaporator. Water (10 ml) was then added followed by adding 10 ml $CH_2Cl_2$. After vigorously shaking and then standing, the bottom layer was separated out and evaporated and 0.7 gram biodiesel was obtained. If multiplied up this equates to a yield of 2.1 wt % biodiesel based on the weight of the dried tunicate.

(B) Transesterification of Dried Tunicate—Acid Catalysed

A sample of tunicate was freeze-dried. 10 grams of the dried tunicate was suspended in 200 ml methanol containing 0.2 M $H_2SO_4$. The mixture was heated to reflux for 10 hours, during which time it was well stirred. The suspension was cooled, centrifuged and the solution was evaporated. The residue obtained was added to 10 ml water. 10 ml $CH_2Cl_2$ was also added. After vigorously shaking the mixture, it was left to stand. The bottom layer was separated out and evaporated and 0.16 gram biodiesel was obtained (1.6 wt % yield biodiesel based on the weight of the dried tunicate).

Example 7—Farming Method

A subsea structure was assembled in sea waters close to Bergen in the month of May. The structure comprised the following elements which were secured to a longline system which held the elements between the depths of −4 and −20 m below sea level:
(i) hollow grey PVC cylinders (each having a diameter of 40 cm and a length of 50 cm) secured to a rope, placed at each meter along the rope;
(ii) rectangular grey PVC plates (each having a length of 50 cm and a width of 34 cm) secured to a rope, placed at each meter along the rope;
(iii) a black rope with a diameter of 1.2 cm (Rope Polysteel 3-strand, 100% Polypropylene multifilament, 12 MM, Bilteama); and
(iv) a green rope with a diameter of 2 cm (Rope Polysteel 3-strand DANLINE 20 MM, AS Fiskevegn).

Figure 8:
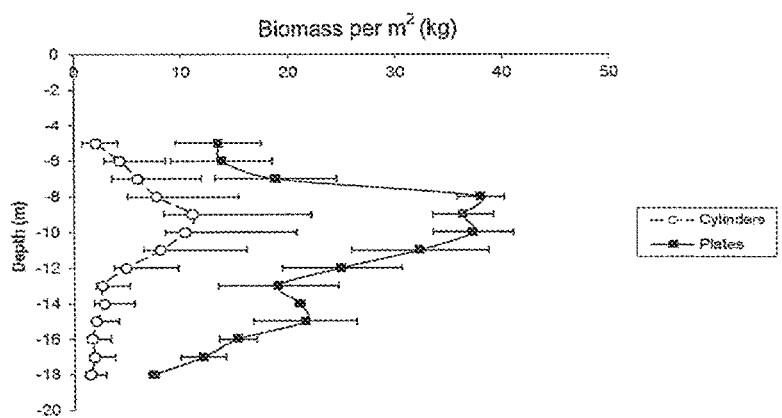
FIG. 8 is a graph of biomass in kg per meter$^2$ as a function of depth (m) of tunicate farmed according to the method of the present invention.
Figure 9:
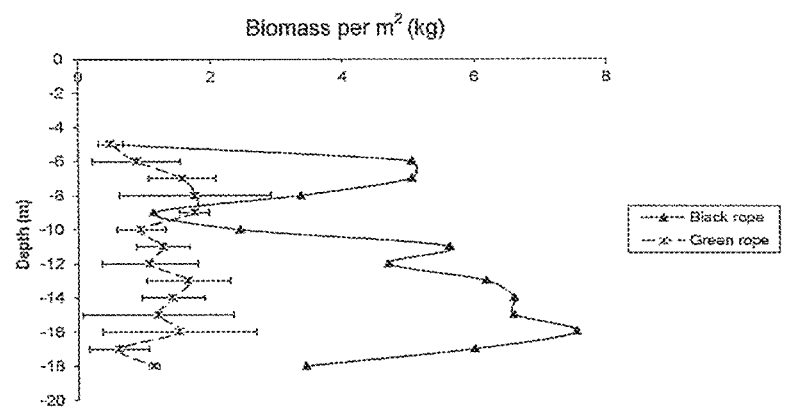
FIG. 9 is a graph of biomass in kg per meter$^2$ as a function of depth (m) of tunicate harvested from ropes of different colours.

Three months later, the ascidians (Ciona intestinalis) were harvested from the subsea structure by pulling the ropes (including those with the cylinders and plates attached) up onto a boat and manually scraping off the ascidians. The biomass collected for every meter of rope was recorded and this was then calculated as a function of surface area. The results are shown in FIGS. 8 and 9. In these figures the biomass in kg per meter$^2$ is shown as a function of depth (m).

The results show that the biomass per meter$^2$ was significantly higher on the ropes with plates attached compared to other ropes. The plates generated an average of 22.2 kg per m$^2$, compared to 4.8 kg on the cylinders, 4.6 kg on the black ropes and finally 1.2 kg on the green ropes. The plates used in this experiment generated an average of 9690 individuals per m$^2$, the cylinders generated 3106 individuals/m$^2$, while the black and green ropes generated 1645 and 529 individuals per m$^2$, respectively.

The black ropes yielded a higher biomass per meter$^2$ than the green ropes, showing that the darker surface favours colonisation and settlement of the ascidians.

Also, it was clear to the eye that both the plate and cylinder structures generated a highly homogenous colonization of Ciona intestinalis with very minor biofouling by other organisms, compared to the black and green ropes.

REFERENCES

1. Matthysse A G, Deschet K, Williams M, et al. W C (2004). Proc. Nat. Acad. Sci. USA 101(4): 986-991.
2. Matthysse A G, Deschet K, Williams M, Marry M, White A R, Smith W C (2004). A functional cellulose synthase from ascidian epidermis. Proceedings of the National Academy of Sciences of the United States of America. 101(4): 986-991.
3. Delsuc F, Brinkmann H, Chourrout D, et al. (2006). Nature. 439(7079): 965-968.
4. Satoh N, Satou Y, Davidson B, et al. (2003). Trend in Genetics. 19(7): 376-381.
5. Dybern B I (1965). Oikos 16: 109-131
6. Swane I, Havenhand J N (1993). Marine Ecology 14(1): 53-66
7. Sasakura Y., K. Nakashima, S. Awazu, et al. 2005. Proc. Natl, Acad. Sci. USA 102: 15134-15139
8. Nakayama-Ishimura A, Chambon J-P, Horei T K, Satoh N, Sasakura Y (2009). Dev. Biol. 326: 357-367
9. Kimura, S., and Itoh, T. (1998). Protoplasma 204, 94-102

10. Li J, Lennholm H, Henriksson G, Gellerstedt G (2000a). 13th International Symposium on Alcohol Fuels (ISAF XIII) (Stockholm, 3-6 July, 2000), proceedings (Vol. I), Number 6
11. Li J, Lennholm H, Henriksson G, Gellerstedt G (2000b). 1st World Conference and Exhibition on Biomass for Energy and Industry (Seville, 5-9 June, 2000), proceedings, 767-770
12. Li J, Lennholm H, Henriksson G, Gellerstedt G (2001). 7th Brazilian Symposium on the Chemistry of Lignins and Other Wood Components, (Belo Horizonte, 3-5 September, 2001), proceedings, 423-430
13. Li J, Lennholm H, Henriksson G, Gellerstedt G (2002). 2nd International Symposium on Emerging Technologies of Pulping & Papermaking, (Guangzhou, 9-11 October, 2002), proceedings, 82-90
14. Lin Y, Tanaka S (2005), *Appl. Microb Biotech* 69(6): 627-642
15. Hahn-Hägerdal B, Galbe M, Gorwa-Grauslund M F, et al. (2006). *Trends in Biotechnology* 24(12): 549-556
16. Carver C E, Chisholm A, Mallet A L (2003). *J. Shellfish res.* 22(3): 621-631.
17. Howes S, Herbinger C M, Darnell P, et al (2006). *Journal of Experimental Marine Biology and Ecology* 342(1): 85-92.
18. Sanderson K (2006). A field in ferment. *Nature.* 444 (7120): 673-676.
19. Kolomaznik K, Klein K, Vasek V, et at (2009). Int. Appl., WO 2009089802

The invention claimed is:

1. A method for farming ascidians in a sea comprising the steps of:
   (a) colonizing surfaces of a sub-sea structure with ascidians; and
   (b) harvesting said ascidians from said structure, wherein said structure comprises a plurality of elongate members and said structure defines a three-dimensional sub-sea region arranged to support ascidian colonization, and further wherein at least one of the plurality of elongate members comprises an elongate support member and a plurality of colonization members, wherein each colonization member is coupled to said support member and comprises at least one uninterrupted planar colonization surface which supports colonization and growth of said ascidians and which is without substantive ridge or projection across an entire horizontal extent of the colonization member relative to the elongate support member.

2. The method for farming ascidians according to claim 1 wherein the at least one uninterrupted planar colonization surface is substantially smooth.

3. The method of farming ascidians according to claim 2 wherein the colonization members are cylinders.

4. The method of farming ascidians according to claim 1 wherein the at least one colonization surface is horizontal.

5. The method according to claim 1 wherein the at least one elongate support member supports the plurality of colonization members, and wherein the plurality of colonization members comprise generally radially extending uninterrupted planar colonization surfaces or members.

6. The method according to claim 5 wherein the generally radially extending colonization surfaces or members are disk or rectangular-shaped, or cylinder-shaped.

7. The method according to claim 1 wherein the colonization surfaces or members are dark in color.

8. The method according to claim 1 wherein the ascidian is *Ciona intestinalis*.

9. A method for farming ascidians comprising:
providing a sub-sea structure which defines a three-dimensional sub-sea region arranged to support tunicate colonization, the sub-sea structure comprising:
   a plurality of elongate support members;
   a plurality of colonization members coupled to each of the elongate support members, each of the colonization members comprising at least one uninterrupted planar colonization surface which is without substantive ridge or projection across an entire horizontal extent of each colonization member of the plurality of colonization members relative to its respective elongate support member;
positioning the sub-sea structure in a sea and orienting the plurality of elongate support members substantially vertically at least in part by at least one buoy;
colonizing surfaces of the sub-sea structure including the at least one uninterrupted planar colonization surface with a monoculture of ascidians; and
harvesting said ascidians from said structure.

10. The method of farming ascidians according to claim 9, wherein the plurality of elongate support members comprise at least one of a (1) rope, (2) a rod, (3) a hollow cylinder, and (4) a combination of (1) (3).

11. The method of farming ascidians according to claim 9, wherein the plurality of elongate support members are coupled to a line which is attached to the at least one buoy, the at least one buoy being a sea-level buoy, and ends of the line being attached to a sea bed.

12. The method of farming ascidians according to claim 9, wherein the plurality of colonization members comprise two or more of the following colonization member types: (1) a disk plate, (2) a cylinder; (3) a rectangular plate.

13. The method of farming ascidians according to claim 12, wherein the plurality of the colonization members are vertically spaced apart on the respective elongate support member by at least 20 cm.

14. The method of farming ascidians according to claim 12, wherein all colonization members attached to the elongate support member are of a same colonization member type.

15. The method of farming ascidians according to claim 12, wherein at least one of the plurality of elongate support members has coupled thereto colonization members of a differing colonization member type than an adjacent elongate support member.

16. The method of farming ascidians according to claim 9, wherein the uninterrupted planar surface of each colonization member of the plurality of colonization members extends circumferentially and radially around a coupling to each of the elongate support members to allow unrestricted access to the uninterrupted planar surface.

17. The method of farming ascidians according to claim 9, wherein the sub-sea structure comprises between 5,000 and 15,000 elongate members.

18. The method of farming ascidians according to claim 9, wherein the plurality of elongate members are between 5 and 70 meters in length.

19. The method of farming ascidians according to claim 9, wherein the sub-sea structure is configured to occupy an ocean surface area of between 5,000 meter$^2$ to 1,000,000 meter$^2$.

20. The method of farming ascidians according to claim 19, further comprising selectively placing the sub-sea structure in nutrient rich waters of the sea with large nutrient inputs from human activities.

21. The method of farming ascidians according to claim 9, further comprising selectively placing the sub-sea structure in nutrient rich waters of the sea.

22. The method of farming ascidians according to claim 9, wherein the colonization member is plastic and wherein the uninterrupted planar surface of the colonization member is solid with no perforation.

* * * * *